United States Patent
Baril et al.

(10) Patent No.: US 11,369,352 B2
(45) Date of Patent: Jun. 28, 2022

(54) DUAL CHANNEL DESIGN FOR FREE STANDING SPECIMEN BAG

(71) Applicant: Covidien LP, Mansfield, MA (US)

(72) Inventors: Jacob C. Baril, Norwalk, CT (US); Saumya Banerjee, Hamden, CT (US)

(73) Assignee: Covidien LP, Mansfield, MA (US)

( * ) Notice: Subject to any disclaimer, the term of this patent is extended or adjusted under 35 U.S.C. 154(b) by 38 days.

(21) Appl. No.: 16/835,499

(22) Filed: Mar. 31, 2020

(65) Prior Publication Data

US 2021/0298729 A1 Sep. 30, 2021

(51) Int. Cl.
*A61B 17/00* (2006.01)

(52) U.S. Cl.
CPC ........ *A61B 17/00234* (2013.01); *A61B 2017/00287* (2013.01)

(58) Field of Classification Search
CPC ........ A61B 17/00234; A61B 17/221; A61B 2017/00287; A61B 2017/00358; A61B 2017/2212
See application file for complete search history.

(56) References Cited

U.S. PATENT DOCUMENTS

| | | | |
|---|---|---|---|
| 6,059,793 A | 5/2000 | Pagedas | |
| 6,156,055 A | 12/2000 | Ravenscroft | |
| 6,162,209 A | 12/2000 | Gobron et al. | |
| 6,171,317 B1 | 1/2001 | Jackson et al. | |
| 6,206,889 B1 | 3/2001 | Bennardo | |
| 6,224,612 B1 | 5/2001 | Bates et al. | |
| 6,228,095 B1 | 5/2001 | Dennis | |
| 6,248,113 B1 | 6/2001 | Fina | |
| 6,258,102 B1 | 7/2001 | Pagedas | |
| 6,264,663 B1 | 7/2001 | Cano | |
| 6,270,505 B1 | 8/2001 | Yoshida et al. | |
| 6,280,451 B1 | 8/2001 | Bates et al. | |
| 6,344,026 B1 | 2/2002 | Burbank et al. | |
| 6,350,266 B1 | 2/2002 | White et al. | |
| 6,350,267 B1 | 2/2002 | Stefanchik | |
| 6,358,198 B1 | 3/2002 | Levin et al. | |
| 6,368,328 B1 | 4/2002 | Chu et al. | |
| 6,383,195 B1 | 5/2002 | Richard | |
| 6,383,197 B1 | 5/2002 | Conlon et al. | |
| 6,387,102 B2 | 5/2002 | Pagedas | |
| 6,406,440 B1 | 6/2002 | Stefanchik | |
| 6,409,733 B1 | 6/2002 | Conlon et al. | |
| 6,447,523 B1 | 9/2002 | Middleman et al. | |

(Continued)

*Primary Examiner* — Mohamed G Gabr
(74) *Attorney, Agent, or Firm* — Carter, DeLuca & Farrell LLP

(57) ABSTRACT

A tissue specimen retrieval bag assembly includes a tissue specimen bag having an open proximal end including a cuff defined therein and extending around a periphery thereof, a closed distal end and a bag brim disposed within the cuff. The bag brim includes a cross section configured to facilitate furling the tissue specimen bag onto itself around the bag brim to approximate a tissue specimen contained within the bag for morcellation. The tissue specimen bag also includes a suture channel defined therein near the proximal end thereof. The suture channel is defined around the periphery of the tissue specimen bag and is configured to house a suture therein. Pulling the suture away from the tissue specimen bag cinches the tissue specimen bag to secure the tissue specimen therein.

15 Claims, 5 Drawing Sheets

(56) References Cited

U.S. PATENT DOCUMENTS

| | | |
|---|---|---|
| 6,530,923 B1 | 3/2003 | Dubrul et al. |
| 6,537,273 B1 | 3/2003 | Sosiak et al. |
| 6,752,822 B2 | 6/2004 | Jespersen |
| 6,805,699 B2 | 10/2004 | Shimm |
| 6,951,533 B2 | 10/2005 | Foley |
| 6,986,774 B2 | 1/2006 | Middleman et al. |
| 7,037,275 B1 | 5/2006 | Marshall et al. |
| 7,052,501 B2 | 5/2006 | McGuckin, Jr. |
| 7,087,062 B2 | 8/2006 | Dhindsa |
| 7,101,379 B2 | 9/2006 | Gregory, Jr. et al. |
| 7,101,380 B2 | 9/2006 | Khachin et al. |
| 7,112,172 B2 | 9/2006 | Orban, III et al. |
| 7,115,125 B2 | 10/2006 | Nakao et al. |
| 7,144,400 B2 | 12/2006 | Byrum et al. |
| 7,169,154 B1 | 1/2007 | Que et al. |
| 7,229,418 B2 | 6/2007 | Burbank et al. |
| 7,285,126 B2 | 10/2007 | Sepetka et al. |
| 7,316,692 B2 | 1/2008 | Huffmaster |
| 7,357,801 B2 | 4/2008 | Burbank et al. |
| 7,534,252 B2 | 5/2009 | Sepetka et al. |
| 7,547,310 B2 | 6/2009 | Whitfield |
| 7,615,013 B2 | 11/2009 | Clifford et al. |
| 7,618,437 B2 | 11/2009 | Nakao |
| 7,654,283 B2 | 2/2010 | Seto et al. |
| 7,670,346 B2 | 3/2010 | Whitfield |
| 7,678,118 B2 | 3/2010 | Bates et al. |
| 7,722,626 B2 | 5/2010 | Middleman et al. |
| 7,727,227 B2 | 6/2010 | Teague et al. |
| 7,731,722 B2 | 6/2010 | Lavelle et al. |
| 7,731,723 B2 | 6/2010 | Kear et al. |
| 7,762,959 B2 | 7/2010 | Bilsbury |
| 7,762,960 B2 | 7/2010 | Timberlake et al. |
| 7,875,038 B2 | 1/2011 | Que et al. |
| 7,892,242 B2 | 2/2011 | Goldstein |
| 7,914,540 B2 | 3/2011 | Schwartz et al. |
| 7,918,860 B2 | 4/2011 | Leslie et al. |
| 7,955,292 B2 | 6/2011 | Leroy et al. |
| 8,057,485 B2 | 11/2011 | Hollis et al. |
| 8,075,567 B2 | 12/2011 | Taylor et al. |
| 8,118,816 B2 | 2/2012 | Teague |
| 8,152,820 B2 | 4/2012 | Mohamed et al. |
| 8,172,772 B2 | 5/2012 | Zwolinski et al. |
| 8,211,115 B2 | 7/2012 | Cheng et al. |
| 8,282,572 B2 | 10/2012 | Bilsbury |
| 8,337,510 B2 | 12/2012 | Rieber et al. |
| 8,348,827 B2 | 1/2013 | Zwolinski |
| 8,409,216 B2 | 4/2013 | Parihar et al. |
| 8,414,596 B2 | 4/2013 | Parihar et al. |
| 8,419,749 B2 | 4/2013 | Shelton, IV et al. |
| 8,425,533 B2 | 4/2013 | Parihar et al. |
| 8,430,826 B2 | 4/2013 | Uznanski et al. |
| 8,435,237 B2 | 5/2013 | Bahney |
| 8,444,655 B2 | 5/2013 | Parihar et al. |
| 8,486,087 B2 | 7/2013 | Fleming |
| 8,512,351 B2 | 8/2013 | Teague |
| 8,579,914 B2 | 11/2013 | Menn et al. |
| 8,585,712 B2 | 11/2013 | O'Prey et al. |
| 8,591,521 B2 | 11/2013 | Cherry et al. |
| 8,652,147 B2 | 2/2014 | Hart |
| 8,721,658 B2 | 5/2014 | Kahle et al. |
| 8,734,464 B2 | 5/2014 | Grover et al. |
| 8,777,961 B2 | 7/2014 | Cabrera et al. |
| 8,795,291 B2 | 8/2014 | Davis et al. |
| 8,821,377 B2 | 9/2014 | Collins |
| 8,827,968 B2 | 9/2014 | Taylor et al. |
| 8,870,894 B2 | 10/2014 | Taylor et al. |
| 8,906,035 B2 | 12/2014 | Zwolinski et al. |
| 8,956,370 B2 | 2/2015 | Taylor et al. |
| 8,968,329 B2 | 3/2015 | Cabrera |
| 8,986,321 B2 | 3/2015 | Parihar et al. |
| 9,005,215 B2 | 4/2015 | Grover et al. |
| 9,017,328 B2 | 4/2015 | Bahney |
| 9,017,340 B2 | 4/2015 | Davis |
| 9,033,995 B2 | 5/2015 | Taylor et al. |
| 9,084,588 B2 | 7/2015 | Farascioni |
| 9,101,342 B2 | 8/2015 | Saleh |
| 9,113,848 B2 | 8/2015 | Fleming et al. |
| 9,113,849 B2 | 8/2015 | Davis |
| 9,308,008 B2 | 4/2016 | Duncan et al. |
| 9,364,201 B2 | 6/2016 | Orban, III |
| 9,364,202 B2 | 6/2016 | Menn et al. |
| 9,370,341 B2 | 6/2016 | Ceniccola et al. |
| 9,370,378 B2 | 6/2016 | O'Prey et al. |
| 9,375,224 B2 | 6/2016 | Jansen |
| 9,414,817 B2 | 8/2016 | Taylor et al. |
| 9,468,542 B2 | 10/2016 | Hurley et al. |
| 9,486,188 B2 | 11/2016 | Secrest et al. |
| 9,522,034 B2 | 12/2016 | Johnson et al. |
| 9,549,747 B2 | 1/2017 | Carlson |
| 9,579,115 B2 | 2/2017 | Kahle et al. |
| 9,592,067 B2 | 3/2017 | Hartoumbekis |
| 9,622,730 B2 | 4/2017 | Farascioni |
| 9,624,638 B2 | 4/2017 | Lebreton et al. |
| 9,629,618 B2 | 4/2017 | Davis et al. |
| 9,655,644 B2 | 5/2017 | Collins |
| 9,730,716 B2 | 8/2017 | Secrest et al. |
| 9,789,268 B2 | 10/2017 | Hart et al. |
| 9,808,228 B2 | 11/2017 | Kondrup et al. |
| 9,826,997 B2 | 11/2017 | Cherry et al. |
| 9,867,600 B2 | 1/2018 | Parihar et al. |
| 9,877,893 B2 | 1/2018 | Taylor et al. |
| 2006/0229640 A1* | 10/2006 | Whitfield ............. A61B 17/221 606/114 |
| 2016/0100857 A1* | 4/2016 | Wachli ............... A61B 17/3423 600/204 |
| 2017/0049427 A1* | 2/2017 | Do ..................... A61B 17/3423 |
| 2019/0142456 A1 | 5/2019 | Wachli et al. |

\* cited by examiner

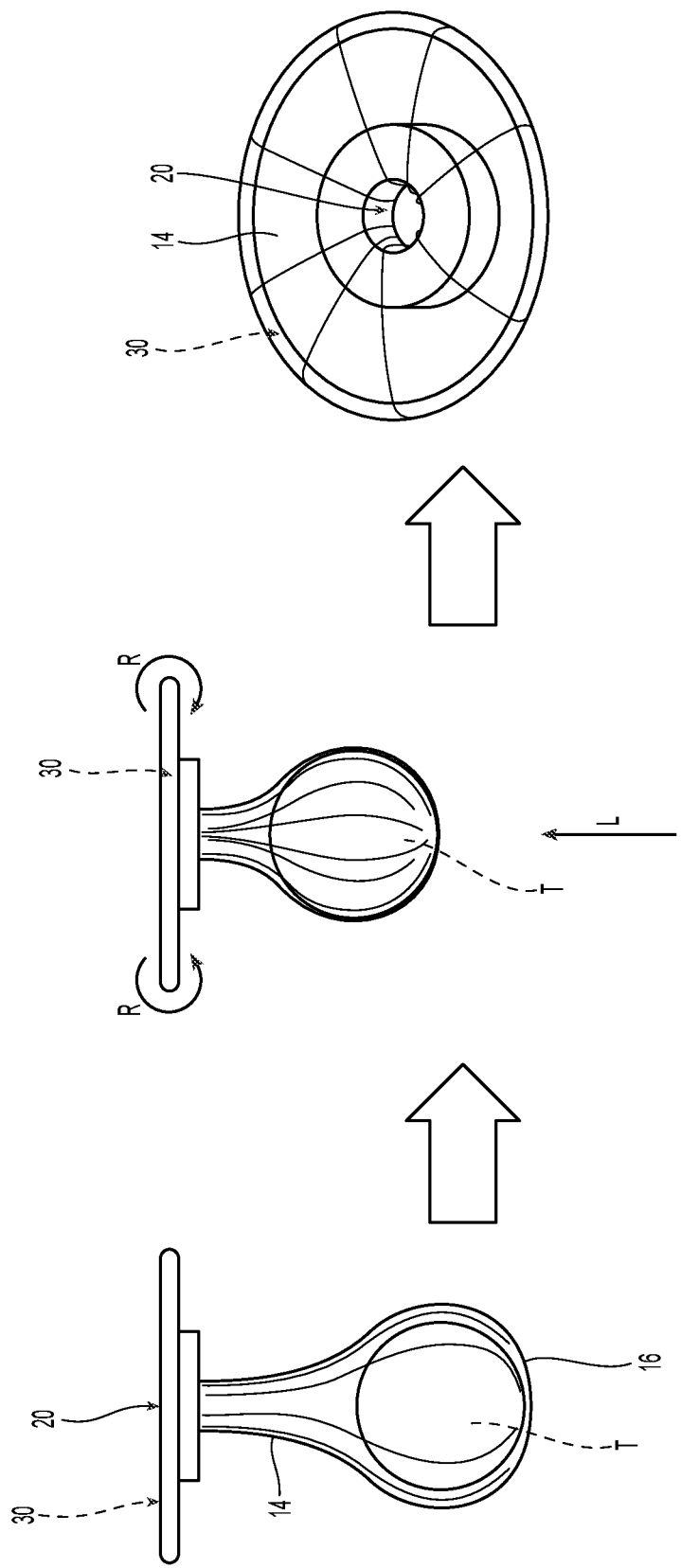

DUAL CHANNEL DESIGN FOR FREE STANDING SPECIMEN BAG

BACKGROUND

Technical Field

The present disclosure relates to tissue specimen retrieval from an internal body cavity and, more particularly, to specimen retrieval or specimen containment bags that facilitate retrieval of a tissue specimen from an internal body cavity.

Background of Related Art

In minimally-invasive surgical procedures, operations are carried out within an internal body cavity through small entrance openings in the body. The entrance openings may be natural passageways of the body or may be surgically created, for example, by making a small incision into which an access device is inserted.

Minimally-invasive surgical procedures may be used for partial or total retrieval of a tissue specimen from an internal body cavity. However, the restricted access provided by minimally-invasive openings (natural passageways and/or surgically created openings) presents challenges with respect to maneuverability and visualization. The restricted access also presents challenges when the tissue specimen is required to be removed. As such, a tissue specimen that is deemed too large for intact retrieval may be broken down into a plurality of smaller pieces to facilitate retrieval from the internal body cavity.

During such minimally-invasive surgical procedures, it is common that a cyst, tumor, or other affected tissue specimen is required to be removed. In these and other procedures where cancerous tissue is required to be removed, retrieval of the tissue specimen in an enclosed environment such as a specimen retrieval bag or containment bag is highly desirable to inhibit seeding of cancer cells. Thus, with respect to breaking down large tissue specimens for retrieval through minimally-invasive openings, there is the added challenge of doing so within an enclosed environment.

In these instances, a standalone tissue bag may be utilized to contain large tissue specimens such as a uterus for hysterectomies or fibroids for myomectomies. The specimen retrieval bag or containment bag typically includes a bag brim having a flexible wire support that is transitionable between a first collapsed configuration for insertion through an incision or natural body orifice and a second expanded configuration for encapsulating tissue specimens. The bag brim, once externalized, may be manipulated or rolled to enhance surgical access to the tissue specimen or "tent" the specimen as needed.

SUMMARY

As used herein, the term "distal" refers to the portion that is described which is further from a user, while the term "proximal" refers to the portion that is being described which is closer to a user. The terms "substantially" and "approximately," as utilized herein, account for industry-accepted material, manufacturing, measurement, use, and/or environmental tolerances. Further, any or all of the aspects and features described herein, to the extent consistent, may be used in conjunction with any or all of the other aspects and features described herein.

In accordance with aspects of the present disclosure is a tissue specimen retrieval bag assembly which includes a tissue specimen bag having an open proximal end including a cuff defined therein and extending around a periphery thereof, a closed distal end and a bag brim disposed within the cuff. The bag brim includes a cross section configured to facilitate furling the tissue specimen bag onto itself around the bag brim to approximate a tissue specimen contained within the bag for morcellation. The tissue specimen bag also includes a suture channel defined therein near the proximal end thereof. The suture channel is defined around the periphery of the tissue specimen bag and is configured to house a suture therein. Pulling the suture away from the tissue specimen bag cinches the tissue specimen bag to secure the tissue specimen therein.

In aspects according to the present disclosure, the tissue specimen bag is made from at least one of nylon or polyurethane.

In other aspects according to the present disclosure, the tissue specimen bag further includes a cinch tab operably engaged with at least one end of the suture to facilitate cinching the tissue specimen bag. In yet other aspects according to the present disclosure, the cinch tab includes a grommet defined therein configured to operably engage the suture. In still other aspects according to the present disclosure, the cinch tab includes a loop defined therein configured to facilitate handling thereof. In yet other aspects according to the present disclosure, the loop is configured and sized to accommodate a user's finger to enhance leverage when cinching.

In aspects according to the present disclosure, the cinch tab is configured to slide atop the suture to lock the tissue specimen bag when cinched.

In accordance with additional aspects of the present disclosure is a tissue specimen retrieval bag assembly which includes a tissue specimen bag having an open proximal end having a cuff defined therein and extending around a periphery thereof, a closed distal end, a bag brim disposed within the cuff. The tissue specimen bag also includes a suture channel defined therein near the proximal end thereof. The suture channel is defined around the periphery of the tissue specimen bag and is configured to house a suture therein. Pulling the suture away from the tissue specimen bag cinches the tissue specimen bag to secure the tissue specimen therein.

In aspects according to the present disclosure, the tissue specimen bag is made from at least one of nylon or polyurethane.

In other aspects according to the present disclosure, the tissue specimen bag further includes a cinch tab operably engaged with at least one end of the suture to facilitate cinching the tissue specimen bag. In yet other aspects according to the present disclosure, the cinch tab includes a grommet defined therein configured to operably engage the suture. In still other aspects according to the present disclosure, the cinch tab includes a loop defined therein configured to facilitate handling thereof. In yet other aspects according to the present disclosure, the loop is configured and sized to accommodate a user's finger to enhance leverage when cinching.

In aspects according to the present disclosure, the cinch tab is configured to slide atop the suture to lock the tissue specimen bag when cinched.

BRIEF DESCRIPTION OF THE DRAWINGS

The above and other aspects and features of the present disclosure will become more apparent in view of the following detailed description when taken in conjunction with the accompanying drawings wherein like reference numerals identify similar or identical elements.

FIGS. 3A-3C are various views of the tissue specimen retrieval bag of FIG. 1 for use with a tissue specimen "T";

DETAILED DESCRIPTION

Figure 1A:
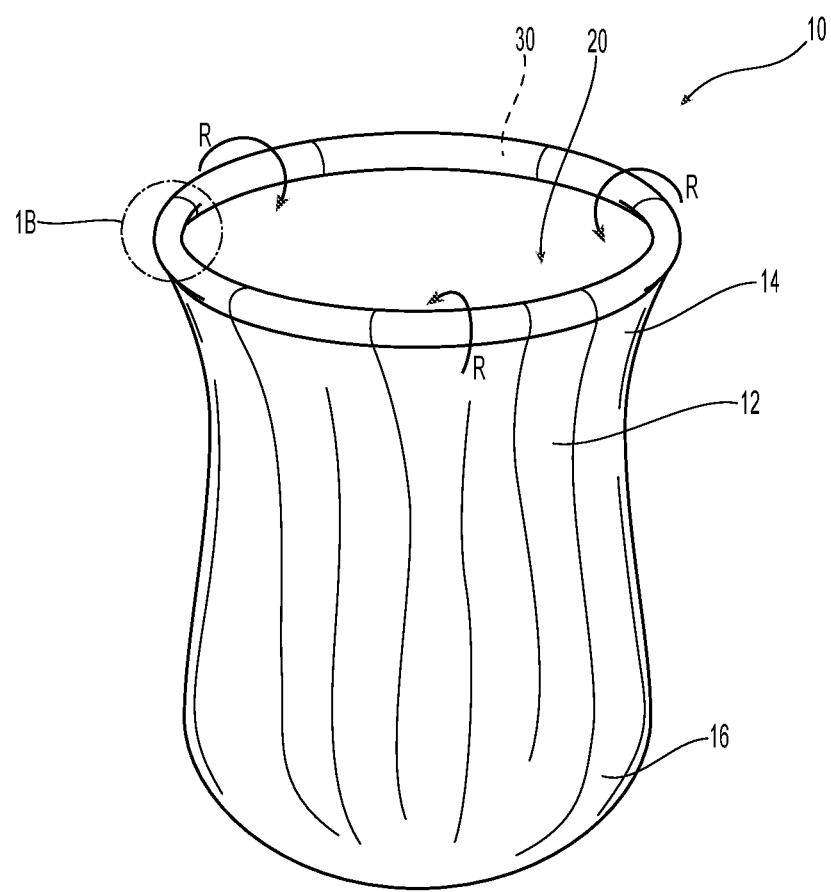
FIG. 1A is a perspective view of a tissue specimen bag provided in accordance with aspects of the present disclosure.
Figure 1B:
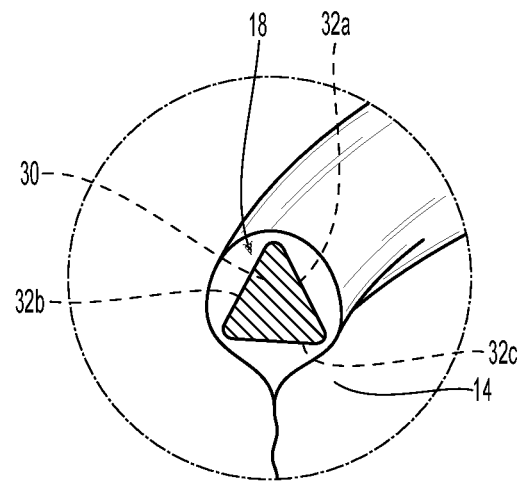
FIG. 1B is a perspective cross sectional view of a proximal end of the tissue specimen bag of FIG. 1A.

Turning initially to FIGS. 1A-1B, one embodiment of a standalone tissue specimen retrieval bag or tissue containment bag assembly is shown and is represent by reference numeral 10. Bag assembly 10 includes a bag 12 having a proximal end 14 including an opening 20 defined therein and an enclosed distal end 16. Bag assembly 10 includes bag rim 30 that is configured to support bag 12 in such a fashion as to define opening 20 when the bag 12 is unfurled or in an open configuration. Opening 20 is of sufficient dimension to receive one or more tissue specimens "T" during a particular surgical procedure. Bag assembly 10 may be made from nylon and/or polyurethane.

Bag rim 30 is configured to be flexible such that the bag brim 30 is easily transitionable between a first, collapsed configuration wherein the bag 12 is furled (as explained below) and a second, expanded configuration which allows the bag 12 to be unfurled for receipt of a tissue specimen "T". As such, bag brim 30 may be made from any flexible material that is easily expandable from a collapsed configuration. Bag 12 may include any suitable rollable material such as nylon, polyurethane, etc.

Bag brim 30 is configured to seat within an elongated cuff 18 (FIG. 1B) defined in the proximal end of the bag 12. More particularly, bag brim 30 is of sufficient dimension to fit within the cuff 18 along an entire length thereof. Bag brim 30 may include two mating ends that, when engaged, form a generally circular configuration when opened to support bag 12 thereon. Bag brim 30 may be generally triangular in shape to include three sides 32a, 32b and 32c. Other geometric configurations or multi-sided arrangements are also envisioned and may be tailored for a particular purpose.

The generally triangular shape of the bag brim 30 allows the bag 12 to roll or furl around itself which, in turn, allows a surgeon to tent (i.e., position) the tissue specimen "T" closer to the proximal end of the operating cavity as needed for dissection. More particularly, the geometry of the sides 32a, 32b and 32c of the bag brim 30 facilitate furling/unfurling the bag 12 as needed and securing the bag 12 in a desired furled position. Although generally illustrated in the various embodiments described herein as being rolled or furled inwardly, it is contemplated that the bag 12 may be rolled either inwardly or outwardly about the bag brim 30.

In use, the specimen "T" is placed into the specimen bag 12 through opening 20. The weight of the specimen "T" causes the specimen "T" to fall to toward the distal end 16 of the bag 12. The proximal end 14 of the bag 12 and the circularly-shaped bag brim 30 maintain the proximal end 14 the bag 12 outside the operating cavity (See for example, FIG. 2). If the surgeon desires to bring the specimen "T" closer to the proximal end 14 of the bag 12, the surgeon furls the bag 12 around the bag brim 30 in the direction "R". The triangular shape of the bag brim 30 facilitates furling the bag 12 and the brim 30 over on itself which, in turn, allows the surgeon to position the tissue specimen "T" at a desired depth within the surgical cavity depending upon a particular purpose. The sides 32a, 32b and 32c of the bag brim 30 may include a high friction surface to facilitate gripping the bag 12 when furling.

Figure 2:
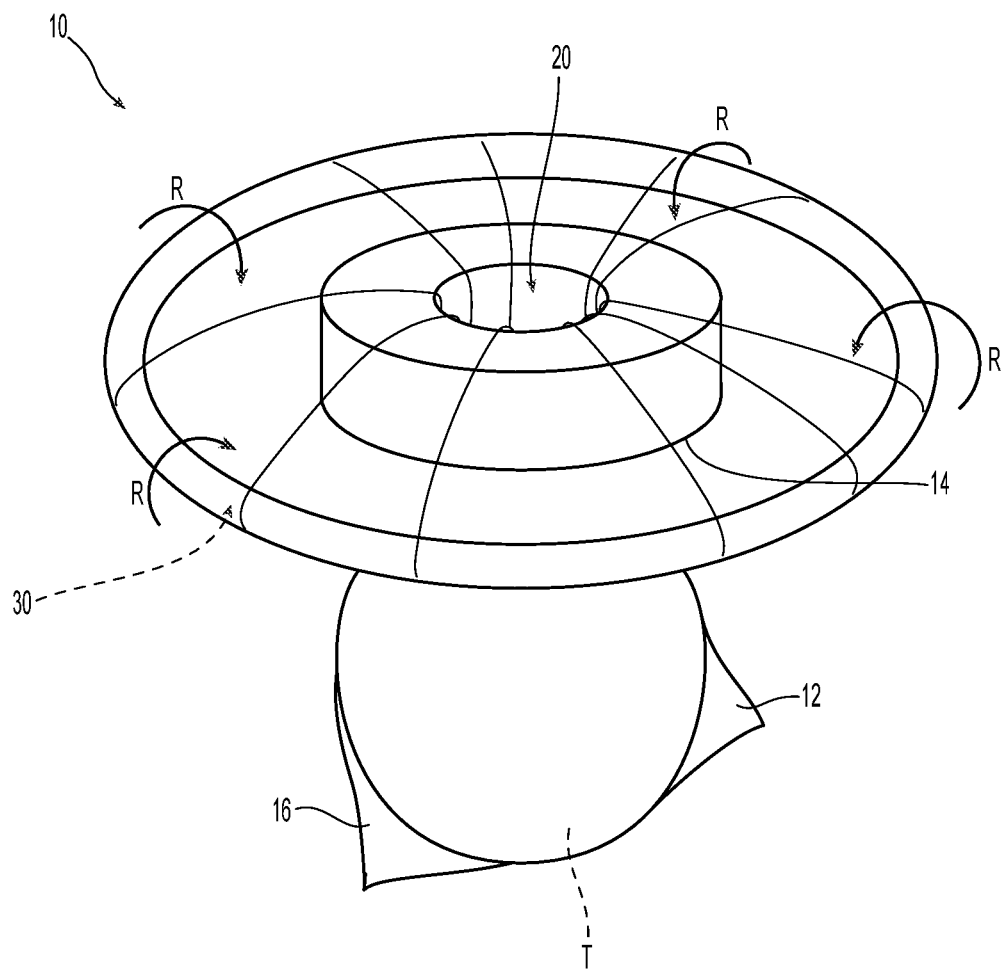
FIG. 2 is a perspective view of the tissue specimen retrieval bag having a rollable bag brim according to the present disclosure.

FIG. 2 shows the tissue specimen retrieval bag assembly 10 in use containing and supporting tissue specimens "T" within a surgical cavity. More particularly, bag assembly 10 includes a bag brim 30 having a bag 12 that depends therefrom for containing a tissue specimen "T". Bag brim 30 is disposed within a cuff (not shown) defined in a proximal end 14 of the bag 12. Bag brim 30 allows the bag 12 to roll or furl around itself which, in turn, allows a surgeon to tent (i.e., position) the tissue specimen "T" closer to the proximal end of the operating cavity as needed for dissection.

More particularly, and as best shown in FIGS. 3A-3C, the geometry of the sides of the bag brim 30 facilitate furling/unfurling the bag 12 as needed and securing the bag 12 in a desired furled position. As shown in FIG. 3A, the specimen "T" is place into the specimen bag 12 through opening 20. The weight of the specimen "T" causes the specimen "T" to fall to toward the distal end 16 of the bag 12. The proximal end 14 of the bag 12 and the circularly-shaped bag brim 30 maintain the proximal end 14 the bag 12 outside the operating cavity (See FIG. 3C). If the surgeon desires to bring the specimen "T" closer to the proximal end 14 of the bag 12, e.g., for morcellation purposes, the surgeon furls the bag 12 around the bag brim 30 in the direction "R". The shape of the bag brim 30 facilitates furling the bag 12 and the brim 30 over on itself which, in turn, allows the surgeon to position the tissue specimen "T" at a desired depth "L" within the surgical cavity depending upon a particular purpose (See FIG. 3B).

FIGS. 4A-6 show another embodiment of tissue specimen retrieval bag assembly 100 for containing and supporting tissue specimens "T" within a surgical cavity. More particularly, bag assembly 100 includes a bag brim 130 having a bag 112 that depends therefrom for containing a tissue specimen "T". Bag brim 130 is disposed within a cuff 118 defined in a proximal end 114 of the bag 112. Bag brim 130 allows the bag 112 to roll or furl around itself which, in turn, allows a surgeon to tent (i.e., position) the tissue specimen "T" closer to the proximal end of the operating cavity as needed, e.g., for inspection, morcellation, dissection, etc.

Figure 5:
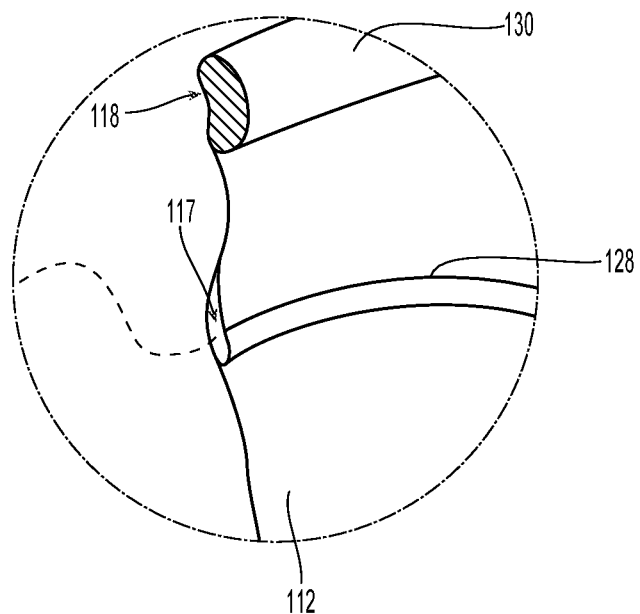
FIG. 5 is an enlarged, perspective, cross sectional view of the tissue specimen retrieval bag of FIGS. 4A-4C.
Figure 6:
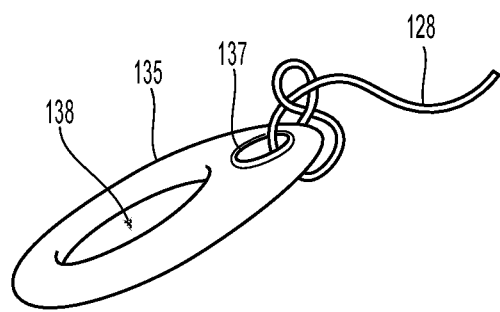
FIG. 6 is an enlarged perspective view of a cinch tab for use with the tissue specimen retrieval bag of FIGS. 4A-4C.

Bag assembly 100 also includes a suture channel 117 defined therein near the proximal end 114 thereof (FIG. 5). Suture channel 117 is defined within the bag 112 around the periphery thereof. Suture channel 117 is configured to house a suture 128 therein such that, after encapsulation of the tissue specimen "T", the suture 128 may be pulled to cinch the bag 112 to contain the specimen "T" for extraction and transport. A cinch tab 135 is utilized to facilitate pulling the suture 128 to cinch the bag 112 (FIG. 6). Cinch tab 135 includes a grommet 137 to reinforce the engagement between the suture 128 and the cinch tab 135.

Figure 4A:
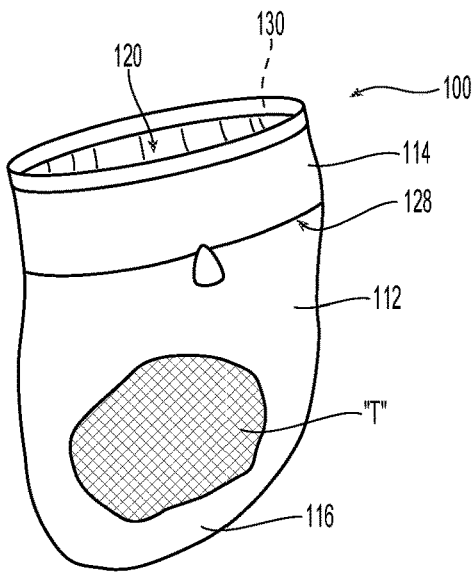
FIG. 4A-4C is a perspective view of another embodiment of a tissue specimen retrieval bag according an embodiment of the present disclosure.
Figure 4B:
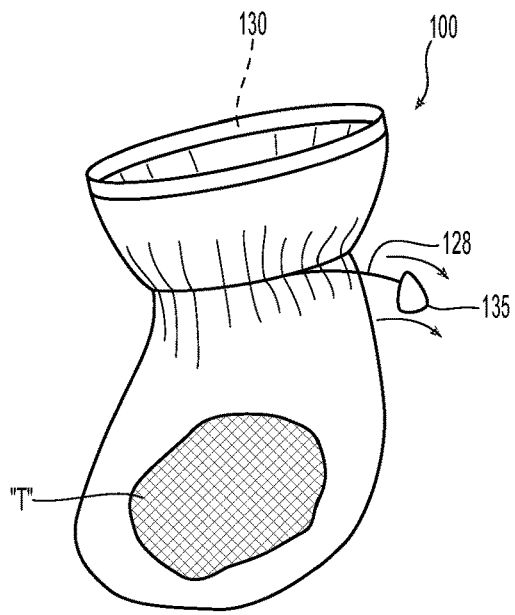
Figure 4C:
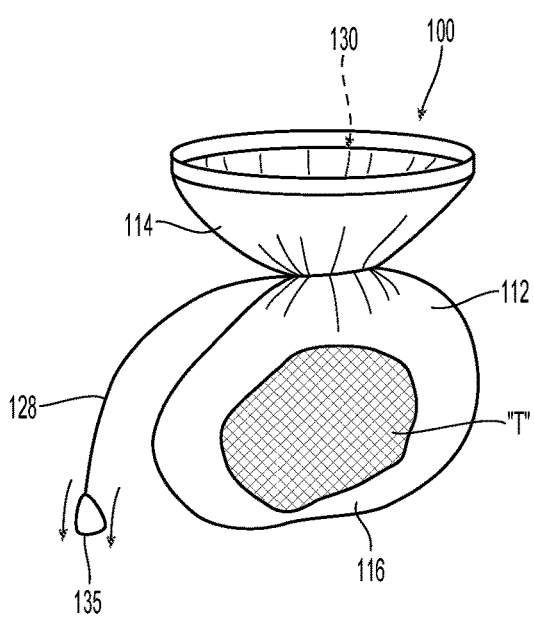

In use and as best shown in FIGS. 4A-4C, a tissue specimen "T" is captured and placed within the bag 112 through opening 120 (FIG. 4A). Additional tissue (not shown) may be added to the bag 112 if needed. Once all of the desired tissue is properly contained within the bag 112, the cinch tab 135 is pulled away from the bag 112 to cinch the proximal end 114 of the bag 112 (FIG. 4B). Continued pulling of the cinch tab 135 away from the bag 112 closes the opening 120 and readies the bag 112 for exteriorization.

After the opening 120 is completely closed, the cinch tab 135 may be slid atop the suture 128 and moved toward the bag 112 to lock the cinch tab 135 against the bag 112 to prevent the bag 112 from re-opening. The grommet 137 may be coated with a high friction material to facilitate this purpose. Alternatively, the cinch tab 135 may include a locking slit (not shown) defined therein such that, once fully seated against the bag 112, the suture 128 can be engaged within the slit to lock the cinch tab 135 in place atop the suture 128. The cinch tab 135 may include a loop 138 defined therein configured to facilitate handling thereof. The loop 138 may be configured and sized to fit a user's finger to enhance a user's grip and provide additional leverage for cinching.

From the foregoing and with reference to the various drawings, those skilled in the art will appreciate that certain modifications can be made to the present disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. A tissue specimen retrieval bag assembly, comprising:
    a tissue specimen bag including:
        an open proximal end having a cuff defined therein and extending around a periphery thereof;
        a closed distal end;
        a bag brim disposed within the cuff, the bag brim having a cross section configured to facilitate furling the tissue specimen bag onto itself around the bag brim by rotating the bag brim to approximate a tissue specimen contained within the bag for morcellation, wherein the bag brim defines a non-circular cross-sectional shape; and
        a suture channel defined therein near the proximal end thereof, the suture channel defined around the periphery of the tissue specimen bag and configured to house a suture therein, wherein pulling the suture away from the tissue specimen bag cinches the tissue specimen bag to secure the tissue specimen therein.

2. The tissue specimen retrieval bag assembly according to claim 1 wherein the tissue specimen bag is made from at least one of nylon or polyurethane.

3. The tissue specimen retrieval bag assembly according to claim 1 further comprising a cinch tab operably engaged with at least one end of the suture to facilitate cinching the tissue specimen bag.

4. The tissue specimen retrieval bag assembly according to claim 3 wherein the cinch tab includes a grommet defined therein configured to operably engage the suture.

5. The tissue specimen retrieval bag assembly according to claim 3 wherein the cinch tab includes a loop defined therein configured to facilitate handling thereof.

6. The tissue specimen retrieval bag assembly according to claim 5 wherein the loop is configured and sized to accommodate a user's finger to enhance leverage when cinching.

7. The tissue specimen retrieval bag assembly according to claim 3 wherein the cinch tab is configured to slide atop the suture to lock the tissue specimen bag when cinched.

8. A tissue specimen retrieval bag assembly, comprising:
    a tissue specimen bag including:
        an open proximal end having a cuff defined therein and extending around a periphery thereof;
        a closed distal end;
        a bag brim disposed within the cuff, the bag brim having a cross section configured to facilitate furling the tissue specimen bag around the cuff by rotating the bag brim to approximate a tissue specimen contained within the bag for morcellation, wherein the bag brim defines at least one of a non-circular cross-sectional shape or a triangular cross-sectional shape; and
        a suture channel defined therein near the proximal end thereof, the suture channel defined around the periphery of the tissue specimen bag and configured to house a suture therein, wherein pulling the suture away from the tissue specimen bag cinches the tissue specimen bag to secure the tissue specimen therein.

9. The tissue specimen retrieval bag assembly according to claim 8 wherein the tissue specimen bag is made from at least one of nylon or polyurethane.

10. The tissue specimen retrieval bag assembly according to claim 8 further comprising a cinch tab operably engaged with at least one end of the suture to facilitate cinching the tissue specimen bag.

11. The tissue specimen retrieval bag assembly according to claim 10 wherein the cinch tab includes a grommet defined therein configured to operably engage the suture.

12. The tissue specimen retrieval bag assembly according to claim 10 wherein the cinch tab includes a loop defined therein configured to facilitate handling thereof.

13. The tissue specimen retrieval bag assembly according to claim 12 wherein the loop is configured and sized to accommodate a user's finger to enhance leverage when cinching.

14. The tissue specimen retrieval bag assembly according to claim 10 wherein the cinch tab is configured to slide atop the suture to lock the tissue specimen bag when cinched.

15. A tissue specimen retrieval bag assembly, comprising:
    a tissue specimen bag including:
        an open proximal end having a cuff defined therein and extending around a periphery thereof;
        a closed distal end;
        a bag brim disposed within the cuff, the bag brim having a cross section configured to facilitate furling the tissue specimen bag onto itself around the bag brim by rotating the bag brim to approximate a tissue specimen contained within the bag for morcellation, wherein the bag brim defines a triangular cross-sectional shape; and
        a suture channel defined therein near the proximal end thereof, the suture channel defined around the periphery of the tissue specimen bag and configured to house a suture therein, wherein pulling the suture away from the tissue specimen bag cinches the tissue specimen bag to secure the tissue specimen therein.

* * * * *